US012543997B2

(12) United States Patent
Kristensen et al.

(10) Patent No.: US 12,543,997 B2
(45) Date of Patent: Feb. 10, 2026

(54) DETERMINATION OF COCHLEAR HYDROPS BASED ON RECORDED AUDITORY ELECTROPHYSIOLOGICAL RESPONSES

(71) Applicant: Interacoustics A/S, Middelfart (DK)

(72) Inventors: Bue Kristensen, Middelfart (DK); Søren Laugesen, Middelfart (DK); Lisbeth Birkelund Simonsen, Middelfart (DK)

(73) Assignee: Interacoustics A/S, Middelfart (DK)

( * ) Notice: Subject to any disclaimer, the term of this patent is extended or adjusted under 35 U.S.C. 154(b) by 973 days.

(21) Appl. No.: 17/347,949

(22) Filed: Jun. 15, 2021

(65) Prior Publication Data

US 2021/0386357 A1 Dec. 16, 2021

(30) Foreign Application Priority Data

Jun. 16, 2020 (EP) .................................... 20180272

(51) Int. Cl.
*A61B 5/00* (2006.01)
*A61B 5/38* (2021.01)

(52) U.S. Cl.
CPC .............. *A61B 5/38* (2021.01); *A61B 5/6815* (2013.01)

(58) Field of Classification Search
None
See application file for complete search history.

(56) References Cited

U.S. PATENT DOCUMENTS

2002/0117176 A1* 8/2002 Mantzaridis ......... A61B 5/1106 128/204.23
2004/0204659 A1* 10/2004 John ........................ A61B 5/38 600/559

(Continued)

FOREIGN PATENT DOCUMENTS

RU 2 722 051 C1 5/2020

OTHER PUBLICATIONS

Kaur et al. Study Of Digital Hearing Aid Using Frequency Shaping Function. International Journal of Engineering Research & Technology. vol. 2, Issue 5, May 2013. (Year: 2013).*

(Continued)

*Primary Examiner* — Etsub D Berhanu
(74) *Attorney, Agent, or Firm* — Birch, Stewart, Kolasch & Birch, LLP

(57) ABSTRACT

The present application relates to a system for diagnosing cochlear hydrops of a person or an animal. The system comprises an acoustic stimulus generating unit comprising a stimulus generator and an output transducer, where the acoustic stimulus generating unit is configured to provide an audio stimulus by the stimulus generator to at least one of the ears of the person or animal via the output transducer, wherein the acoustic stimulus generating unit is configured to provide a plurality of audio stimuli comprising at least a first click audio stimulus and a first chirp audio stimulus or at least a first and a second chirp audio stimuli, a recording unit configured to record one or more auditory electrophysiological response of the person or animal in response to the one or more audio stimulus being provided by the acoustic stimulus generating unit to at least one of the ears of the person or animal, and a diagnostic unit configured to process the recorded ABR.

17 Claims, 3 Drawing Sheets

(56) References Cited

U.S. PATENT DOCUMENTS

2005/0273018 A1* 12/2005 Don ........................ A61B 5/121 600/559
2010/0030096 A1* 2/2010 Bradley .................... A61B 5/38 600/544

OTHER PUBLICATIONS

Iseli et al. A comparison of three methods of using transtympanic electrocochleography for the diagnosis of Meniere's disease: Click summating potential measurements, tone burst summating potential amplitude measurements, and biasing of the summating potential using a low frequency tone. (Year: 2010).*
Elberling et al. Auditory brainstem responses to a chirp stimulus designed from derived-band latencies in normal-hearing subjects. The Journal of the Acoustical Society of America. Nov. 2008. (Year: 2008).*
Elberling et al. Evaluating auditory brainstem responses to different chirp stimuli at three levels of stimulation. The Journal of the Acoustical Society of America. Jul. 2010. (Year: 2010).*
Ferraro et al. SP/AP Area Ratio in the Diagnosis of Meniere's Disease. American Journal of Audiology. vol. B; Jun. 21-28, 1999. (Year: 1999).*
Cebulla et al. Evaluation of waveform, latency and amplitude values of chirp ABR in newborns. International Journal of Pediatric Otorhinolaryngology. 78 (2014) 631-636. (Year: 2014).*
Petoe et al. On chirp stimuli and neural synchrony in the suprathreshold auditory brainstem response. The Journal of the Acoustical Society of America. Jul. 2010. (Year: 2010).*
Ozgur et al. Comparison of Tone Burst, Click and Chirp Stimulation in Vestibular Evoked Myogenic Potential Testing in Healthy People. The Journal of International Advanced Otology. 2015; 11(1): 33-5. (Year: 2015).*
Ying-ying et al. Study of cochlear hydrops analysis masking procedure in patients with Meniere's disease and otologically normal adults. Chinese Medical Journal. 2012; 125(24):4449-4453. (Year: 2012).*
Don et al., "A Diagnostic Test for Ménière's Disease and Cochlear Hydrops: Impaired High-Pass Noise Masking of Auditory Brainstem Responses," Otology & Neurotology, vol. 26, No. 4, 2005, pp. 711-722.
Petoe et al., "A System to Generate Patient-Specific Stimuli for use with the Auditory Brainstem Response Test," Proceedings of the 29th Annual International Conference of the IEEE EMBS Cite Internationale, Lyon, France, Aug. 23-26, 2007, pp. 2452-2455.
English translation of the Chinese Office Action for Chinese Application No. 202110667993.8, dated Apr. 7, 2025.

* cited by examiner

DETERMINATION OF COCHLEAR HYDROPS BASED ON RECORDED AUDITORY ELECTROPHYSIOLOGICAL RESPONSES

SUMMARY

The present application relates to a system for diagnosing cochlear hydrops of a person or an animal.

The present application further relates to a method of recording an auditory electrophysiological response of the person or animal.

A system for Diagnosing Cochlear Hydrops

Meniere's disease is today typically diagnosed by the observing the symptoms episodic vertigo, tinnitus, fluctuating hearing loss, and sensation of fullness of the ear or pressure. Further, sometimes the diagnosis may be combination with a CT or MR scanning to exclude any other causes of the symptoms.

Not all patients show all of the above symptoms and especially in the early stages of the Meniere's disease, only some symptoms may appear.

The cause of Meniere's disease is still not fully understood. However, the proposed etiology of Meniere's disease is endolymphatic (or cochlear) hydrops. Endolymphatic hydrops is a condition where distension of the endolymphatic system occurs [1].

Several methods for identifying the symptoms as stemming from Meniere's disease have been proposed such as:

Vestibular evoked myogenic potentials.

Electrocochleography.

The Cochlear Hydrops Analysis Masking Procedure (CHAMP) [2].

However, each of these methods are associated with different challenges. For example, while CHAMP is reported to reach high sensitivity and specificity for patients with full-blown Meniere's disease, lower sensitivity and specificity are found for patients with early stage Meniere's and an uncertain diagnosis is the result. Further, the CHAMP is laborious.

Further, the process of identifying the symptoms as stemming from Meniere's disease may be long and unpleasant for the patient.

Therefore, a simple and fast objective test of identifying the symptoms as stemming from Meniere's disease is very desirable.

In an aspect of the present application, a system for diagnosing cochlear hydrops of a person or an animal is provided.

The system may comprise an acoustic stimulus generating unit comprising a stimulus generator and an output transducer.

The system may comprise a loudspeaker.

For example, the loudspeaker may comprise the output transducer so that audio from the acoustic stimulus generating unit may be output in the environment of the person or animal.

The system may comprise a headset.

For example, the headset may comprise the output transducer so that audio from the acoustic stimulus generating unit may be output from the headset at the ear(s) of the person or animal.

The system may comprise an ear-contacting part.

For example, the ear-contacting part may be an ear-piece suitable for being inserted into the ear canal of the person or animal. The ear-piece may comprise a flexible material configured to conform with the shape of the wall of the ear canal of the person or animal, such as a dome or mold. The ear-piece may comprise a mold having a shape substantially fitting the shape of the wall of the ear canal of the person or animal.

For example, the output transducer may be arranged in the ear-contacting part so that the output transducer may be located in the ear canal in a stable manner and output the acoustic stimulus correctly towards the inner ear of the person or animal.

The stimulus generator may be connected to the output transducer (and e.g. the ear-contacting part, the loudspeaker, or the headset if present) in a wired or wireless manner.

The acoustic stimulus generating unit may be configured to provide one or more audio stimuli by the stimulus generator to at least one of the ears of the person or animal via the output transducer. For example, the acoustic stimulus generating unit may be configured to automatically provide an audio stimulus by the stimulus generator, whereby a simple audio stimulus generation is provided.

The acoustic stimulus generating unit may be configured to provide a plurality of audio stimuli.

For example, the acoustic stimulus generating unit may be configured to provide two or more different types of audio stimuli so that the response of the person or animal to different audio stimuli may monitored and compared to get more data for the evaluation of the person or animal.

The plurality of audio stimuli may comprise providing at least a first click audio stimulus and at least a first chirp audio stimulus.

The plurality of audio stimuli may comprise providing at least a first chirp audio stimulus and at least a second chirp audio stimulus.

For example, a chirp audio stimulus may comprise a CE-chirp [4].

The system may comprise a recording unit configured to record one or more auditory electrophysiological responses of the person or animal.

The one or more auditory electrophysiological response may be recorded in response to the audio stimulus being provided by the acoustic stimulus generating unit to at least one of the ears of the person or animal.

For example, the acoustic stimulus generating unit may provide the plurality of audio stimuli via the output transducer to the inner ear of the person or animal and may record the resulting one or more auditory electrophysiological responses of the person or animal to each provided audio stimulus.

For example, the system may be configured to (e.g. automatically) record an auditory electrophysiological response of the person or animal in response to one or more audio stimulus being provided by the acoustic stimulus generating unit, whereby a simple recording of auditory electrophysiological response is provided.

For example, the one or more auditory electrophysiological responses may be measured by electrodes arranged at the skin of the person or animal.

For example, the one or more auditory electrophysiological responses may be measured by electrodes arranged at the ear-contacting part of the acoustic stimulus generating unit.

The system may comprise a diagnostic unit.

The diagnostic unit may be configured to process the recorded auditory electrophysiological responses.

For example, processing the recorded auditory electrophysiological response may comprise sorting the recorded auditory electrophysiological response depending on e.g. the type and size of the plurality of audio stimuli.

For example, processing the recorded auditory electrophysiological response may comprise analyzing the recorded auditory electrophysiological response, e.g. determining a parameter (e.g. a size) of the auditory electrophysiological response, such as determining an amplitude of the recorded auditory electrophysiological response.

The diagnostic unit may be configured to provide a diagnosis of cochlear hydrops of the person or animal based on the one or more audio stimuli.

For example, providing a diagnosis of cochlear hydrops may comprise determining whether the person or animal has cochlear hydrops, or not. Providing a diagnosis may be based on the analysis of the auditory electrophysiological response recorded in response to the at least first click audio stimulus and at least first chirp audio stimulus, or in response to the at least first and second chirp audio stimuli.

Accordingly, cochlear hydrops may be diagnosed based on providing at least a first click audio stimulus and at least a first chirp audio stimulus, or on providing at least one first and second chirp audio stimulus, and recording and processing the resulting auditory electrophysiological response, which is faster, easier, and more comfortable to the person or animal compared to existing techniques.

The recorded auditory electrophysiological response may be an auditory brain-stem response (ABR).

The system may comprise a recording unit configured to record one or more ABRs of the person or animal.

The diagnostic unit being configured to process the recorded one or more auditory electrophysiological responses, may comprise that the diagnostic unit may be configured to compare response characteristics (e.g. in time or frequency domain) of the recorded one or more auditory electrophysiological responses based on the at least first click audio stimulus and at least first chirp audio stimulus, respectively, or based on the at least first and second chirp audio stimuli, respectively.

The diagnostic unit being configured to process the recorded one or more auditory electrophysiological responses and provide a diagnosis of cochlear hydrops, may comprise that the diagnostic unit may be configured to compare a response characteristics (e.g. in time or frequency domain) of the recorded one or more auditory electrophysiological responses based on the at least first click audio stimulus and at least first chirp audio stimulus, or based on the at least first and second chirp audio stimuli.

In the CHAMP technique mentioned above, suprathreshold click audio stimuli are generated. The resulting auditory electrophysiological responses are then measured with different amounts of masking and the effect on wave-V latency is examined.

Accordingly, the CHAMP technique involves recording auditory electrophysiological responses to moderate level clicks and simultaneous Ipsilateral high-pass masking noise. Responses to the click audio stimuli presented alone and to click audio stimuli with masking noise high-pass filtered at 8, 4, 2, 1 and 0.5 kHz are recorded.

For a typical normal-hearing test subject without cochlear hydrops a very clear effect of the masking is seen. Here, the latency of wave V in the auditory electrophysiological response is observed to increase as the cut off frequency of the high-pass masking noise is lowered. Typically, the highest unmasked frequency region dominates the latency of wave V. Therefore, as the cochlea is successively masked from 8 kHz down to 0.5 kHz, the peak latency of wave V increases.

The observed increased wave V latency is expected because with each lowering of the high-pass masking noise cut off frequency, the response to the click audio stimuli is dominated by a lower-frequency region. Thus, due to factors related to the cochlear travelling wave delay, the wave V latency of the measured auditory electrophysiological response increases as the area of the unmasked cochlea is successively restricted to lower frequencies.

In contrast, a CHAMP measurement of a person or an animal suffering from Meniere's disease show essentially no effect of masking on wave V latency in the sense that no increase in wave V latency is seen by high-pass masking noise [2].

The diagnostic unit being configured to compare, may comprise that the diagnostic unit may be configured to determine a ratio between the respective response characteristics of the recorded one or more auditory electrophysiological responses based on the at least first click audio stimulus and first chirp audio stimulus.

The diagnostic unit being configured to compare, may comprise that the diagnostic unit may be configured to determine a ratio between the respective response characteristics of the recorded one or more auditory electrophysiological responses based on the at least first and second chirp audio stimuli.

For example, the diagnostic unit may be configured to receive a recorded auditory electrophysiological response, in response to at least a first click audio stimulus is provided to the ear of the person or animal, and determine the corresponding response characteristics. Further, the diagnostic unit may be configured to receive a recorded auditory electrophysiological response, in response to at least a first chirp audio stimulus is provided to the ear of the person or animal, and determine the corresponding response characteristics. Further, the diagnostic unit may be configured to receive a recorded auditory electrophysiological response, in response to at least a second chirp audio stimulus is provided to the ear of the person or animal, and determine the corresponding response characteristics. The diagnostic unit may be configured to determine a ratio between the determined response characteristics of the click and chirp audio stimuli, respectively.

In a normal cochlea, it has been found that higher wave V amplitude can be obtained if the traditional click audio stimulus is replaced by a chirp audio stimulus, for example a CE-Chirp [3][4]. This increased amplitude stems from the mean travelling wave travel time in the healthy cochlea, to which the dispersion of the chirp audio stimulus is aligned to produce optimal synchronous stimulation, which leads to a higher wave V amplitude compared with a click audio stimulus.

The CHAMP measurements suggest that the normal cochlear travel time is severely reduced in an ear of a person or an animal with cochlear hydrops. For a normal hearing person, it usually takes approx. 10 ms for an audio stimulus to travel through the cochlea. Further, there is a difference in travelling time of e.g. 10 ms between a low frequency and a high frequency in the cochlear (depending on the exact frequencies). This suggests that the wave V amplitude benefit of the chirp audio stimulus over the click audio stimulus observed in the ear of a person or an animal with normal hearing would be replaced by a disbenefit in the ear of a person or an animal with cochlear hydrops.

The at least one first chirp audio stimulus may be different from the at least one second chirp audio stimulus.

For example, the first chirp audio stimulus may have a longer or shorter duration than the second chirp audio stimulus.

For example, the first chirp audio stimulus may have a larger or smaller sound pressure level than the second chirp audio stimulus.

By for example designing the first chirp audio stimulus according to the average delay profile of cochleae affected by hydrops, and designing the second chirp audio stimulus according to the average delay profile of healthy cochleae, an improved ability to distinguish can be obtained, compared with the method based on a click and a chirp described above.

The first chirp audio stimulus may have a delay profile (a duration) according to the average delay profile of a cochleae affected by hydrops.

The second chirp audio stimulus may have a delay profile (a duration) according to the average delay profile of a healthy cochleae.

It is contemplated that the delay profiles of the first and second chirp audio stimuli may be the reverse.

By measuring in a sequential of interleaved fashion across different sound pressure levels, a richer data material for comparison will be achieved, possibly leading to a more accurate diagnosis. It is to be understood that at each sound pressure level, a comparison may be made between click and chirp responses, or first and second chirp audio stimulus responses.

This effect may then be used as a simpler diagnosis of cochlear hydrops.

The simplicity comes from two things:

- Only two measurement conditions may be needed, e.g. compared to the six conditions specified for a fully-fledged CHAMP.
- The two measurements required for the proposed technique are both unmasked, which promises a shorter averaging time required e.g. compared with the masked conditions of the CHAMP.

The diagnostic unit may be configured to compare the determined ratio with predetermined ratios.

For example, the diagnostic unit may be configured to determine whether the response characteristics based on the chirp audio stimulus is higher than the response characteristics based on the click audio stimulus. In such a case, the person or animal is diagnosed with a normal hearing.

For example, the diagnostic unit may be configured to determine whether the response characteristics based on the click audio stimulus is higher than the response characteristics based on the chirp audio stimulus. In such a case, the person or animal is diagnosed with cochlear hydrops.

The acoustic stimulus generating unit may be configured to provide the at least first click audio stimulus and at least first chirp audio stimulus at a fixed suprathreshold level.

The acoustic stimulus generating unit may be configured to provide the at least first chirp audio stimulus and at least second chirp audio stimulus at a fixed suprathreshold level.

For example, the click audio stimulus and chirp audio stimulus may be provided at 60 dB.

The click audio stimulus may be frequency shaped.

The click audio stimulus may be frequency shaped based on a hearing threshold level (HTL) of the person or animal.

The chirp audio stimulus (first and/or second) may be frequency shaped.

The chirp audio stimulus may be frequency shaped based on an HTL of the person or animal.

The HTL may be determined based on an audiogram measured on the person or animal at an earlier stage. For example, an earlier stage may be immediately before using the system on the person or animal or at an even earlier stage.

The click audio stimulus and/or the chirp audio stimulus (first and/or second) may be provided at a fixed sensation level (SL).

The click audio stimulus and/or the chirp audio stimulus (first and/or second) may be provided at a fixed SL above the HTL of the person or animal across the stimulus frequency range.

For example, the click audio stimulus and/or the chirp audio stimulus (first and/or second) may be provided at 20 dB SL above the HTL of the person or animal across the stimulus frequency range.

The acoustic stimulus generating unit may be configured to provide a plurality of click audio stimuli and chirp audio stimuli.

The acoustic stimulus generating unit may be configured to provide a plurality of chirp audio stimuli.

The acoustic stimulus generating unit may be configured to provide a plurality of click audio stimuli.

The acoustic stimulus generating unit may be configured to provide a plurality of click audio stimuli and/or chirp audio stimuli to at least one of the ears of the person or animal in an alternating manner.

The acoustic stimulus generating unit may be configured to provide alternating click audio stimuli and/or chirp audio stimuli to at least one of the ears of the person or animal.

The acoustic stimulus generating unit may be configured to provide a plurality of click audio stimuli and/or chirp audio stimuli to both ears of the person or animal in an alternating manner.

The acoustic stimulus generating unit may be configured to provide alternating click audio stimuli and/or chirp audio stimuli to both ears of the person or animal.

For example, the plurality of audio stimuli may be provided simultaneously to both ears of the person or animal in an alternating manner.

For example, the acoustic stimulus generating unit may be configured to provide alternating first click audio stimulus and first chirp audio stimulus.

For example, the acoustic stimulus generating unit may be configured to provide alternating first chirp audio stimulus and second chirp audio stimulus.

Thereby, an even more precise diagnosis of the person or animal may be performed, as measurements at both ears of the person or animal at the same time and under similar conditions may be carried out.

The acoustic stimulus generating unit may be configured to provide a plurality of click audio stimuli at a plurality of sound pressure levels to at least one of the ears of the person or animal.

The acoustic stimulus generating unit may be configured to provide a plurality of chirp audio stimuli at a plurality of sound pressure levels to at least one of the ears of the person or animal.

For example, the plurality of click and/or chirp audio stimuli may be provided at similar sound pressure levels to both ears of the person or animal at the same time to allow ear specific information to be retrieved. Thereby, the audio stimuli provision and the following auditory electrophysiological response recording may be simplified.

For example, the auditory electrophysiological response recordings may be done successively in response to the provided plurality of click and/or chirp audio stimuli to facilitate the following analysis of the recordings.

For example, the auditory electrophysiological response recordings may be done interleaved.

The diagnostic unit may be configured to provide respective averages of the response characteristics of the recorded one or more auditory electrophysiological responses based on at least first click audio stimulus and first chirp audio stimulus, respectively, or based on the at least first and second chirp audio stimuli, respectively.

The diagnostic unit may be configured to provide an average of the response characteristics of the recorded auditory electrophysiological response based on the first click audio stimulus.

The diagnostic unit may be configured to provide an average of the response characteristics of the recorded auditory electrophysiological response based on the first chirp audio stimulus or on the second chirp audio stimulus.

The diagnostic unit may be configured to process the recorded auditory electrophysiological response, including providing respective average response characteristics, and configured to provide a diagnosis of cochlear hydrops of the person or animal based on the respective average first click audio stimulus and average chirp audio stimulus, or based on the respective average first chirp audio stimulus and average second chirp audio stimulus.

The system may be configured to diagnose based on simultaneously measuring on both ears of the person or animal to allow ear specific information to be retrieved.

For example, the acoustic stimulus generating unit of the system may comprise one loudspeaker comprising an output transducer.

For example, the acoustic stimulus generating unit of the system may comprise a headset and two output transducers.

For example, the acoustic stimulus generating unit of the system may comprise two ear-contacting parts and two output transducers. The one ear-contacting part may fit into the left ear and the other ear-contacting part may fit into the right ear of the person or animal. The one output transducer may fit into the one ear-contacting part and the other output transducer may fit into the other ear-contacting part.

Thereby, the acoustic stimulus generating unit may be configured to provide one or more audio stimuli by the stimulus generator to both of the ears of the person or animal simultaneously or alternately via the output transducer(s).

When having only one output transducer, measurements may be done at one ear first and at a second ear next.

The response characteristics may comprise a wave V amplitude of the recorded one or more auditory electrophysiological responses.

The one or more auditory electrophysiological responses may be one or more auditory brain-stem responses (ABR).

The system may be or form part of a portable device, e.g. a device comprising a local energy source, e.g. a battery, e.g. a rechargeable battery.

Use:

In an aspect, use of a system as described above, in the ‘detailed description of embodiments’ and in the claims, is moreover provided.

A method:

In an aspect, a method of recording an auditory electrophysiological response of a person or an animal is furthermore provided by the present application.

The method may comprise providing an audio stimulus.

The audio stimulus may comprise at least a first click audio stimulus.

The audio stimulus may comprise at least a first chirp audio stimulus.

The audio stimulus may comprise at least a second chirp audio stimulus.

The at least first click audio stimulus and/or at least first chirp audio stimulus may be provided by the stimulus generator of an acoustic stimulus generating unit.

The at least first chirp audio stimulus and/or at least second chirp audio stimulus may be provided by the stimulus generator of an acoustic stimulus generating unit.

The at least first click audio stimulus and/or at least first chirp audio stimulus may be provided to at least one of the ears of the person or animal via an output transducer of the acoustic stimulus generating unit.

The at least first chirp audio stimulus and/or at least second chirp audio stimulus may be provided to at least one of the ears of the person or animal via an output transducer of the acoustic stimulus generating unit.

The method may comprise recording one or more auditory electrophysiological response of the person or animal, by a recording unit.

The method may comprise recording one or more auditory electrophysiological response of the person or animal, by a recording unit, in response to the one or more audio stimuli being provided by the acoustic stimulus generating unit to at least one of the ears of the person or animal.

The method may comprise processing the recorded one or more auditory electrophysiological responses.

The method may comprise providing a diagnosis of cochlear hydrops of the person or animal, by a diagnostic unit.

The method may comprise processing the recorded auditory electrophysiological responses, by a diagnostic unit, based on the at least first click audio stimulus and at least first chirp audio stimulus.

The method may comprise processing the recorded auditory electrophysiological response and providing a diagnosis of cochlear hydrops of the person or animal, by a diagnostic unit, based on the at least first click audio stimulus and at least first chirp audio stimulus.

The method may comprise processing the recorded auditory electrophysiological responses, by a diagnostic unit, based on the at least first chirp audio stimulus and at least second chirp audio stimulus.

The method may comprise processing the recorded auditory electrophysiological response and providing a diagnosis of cochlear hydrops of the person or animal, by a diagnostic unit, based on the at least first chirp audio stimulus and at least second chirp audio stimulus.

The method may comprise measuring a hearing threshold level (HTL) of at least one of the ears of the person or animal.

The step of processing the recorded one or more auditory electrophysiological response and providing a diagnosis of cochlear hydrops of the person or animal may comprise comparing response characteristics (e.g. a wave V amplitude) of the recorded one or more auditory electrophysiological responses based on the at least first click audio stimulus and first chirp audio stimulus.

The step of processing the recorded one or more auditory electrophysiological response and providing a diagnosis of cochlear hydrops of the person or animal may comprise comparing response characteristics (e.g. a wave V amplitude) of the recorded one or more auditory electrophysiological responses based on the at least first and second chirp audio stimuli.

The step of comparing may comprise determining a ratio between the respective response characteristics of the recorded one or more auditory electrophysiological responses based on the at least first click audio stimulus and first chirp audio stimulus.

The step of comparing may comprise determining a ratio between the respective response characteristics of the recorded one or more auditory electrophysiological responses based on the at least first and second chirp audio stimulus.

Other methods of evaluating the characteristics of the response instead of measuring the wave V amplitude of the response could be applied. For example, the responses or their differences in the frequency domain could be assess.

The acoustic stimulus generating unit may provide a plurality of click audio stimuli to at least one of the ears of the person or animal.

The acoustic stimulus generating unit may provide a plurality of chirp audio stimuli to at least one of the ears of the person or animal.

Wave V responses are likely to provide the clinically most robust response component for such assessments as described here, but other response components might be used as well, either alone or in combination where the combination may or may not include wave V.

The acoustic stimulus generating unit may provide a plurality of click audio stimuli and/or chirp audio stimuli in an alternating manner to at least one of the ears of the person or animal.

The audio stimulus may have a specified frequency bandwidth.

The audio stimulus may have a specified presentation rate.

The audio stimulus may have a specified amplitude.

The audio stimulus may have a specified spectral content.

The audio stimulus may have a specified frequency bandwidth, presentation rate, amplitude, and spectral content.

It is intended that some or all of the structural features of the system described above, in the 'detailed description of embodiments' or in the claims can be combined with embodiments of the method, when appropriately substituted by a corresponding process and vice versa. Embodiments of the method have the same advantages as the corresponding devices.

A computer readable medium or data carrier:

In an aspect, a tangible computer-readable medium (a data carrier) storing a computer program comprising program code means (instructions) for causing a data processing system (a computer) to perform (carry out) at least some (such as a majority or all) of the (steps of the) method described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Other storage media include storage in DNA (e.g. in synthesized DNA strands). Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

A computer program:

A computer program (product) comprising instructions which, when the program is executed by a computer, cause the computer to carry out (steps of) the method described above, in the 'detailed description of embodiments' and in the claims is furthermore provided by the present application.

A data processing system:

In an aspect, a data processing system comprising a processor and program code means for causing the processor to perform at least some (such as a majority or all) of the steps of the method described above, in the 'detailed description of embodiments' and in the claims is furthermore provided by the present application.

Auxiliary Device:

The system may be adapted to establish a communication link between the system and an auxiliary device to provide that information (e.g. control and status signals, possibly audio signals) can be exchanged or forwarded from one to the other.

The auxiliary device may comprise a remote control, or other portable electronic device.

The auxiliary device may be constituted by or comprise a remote control for controlling functionality and operation of the system, such as via a user interface.

An APP:

In a further aspect, a non-transitory application, termed an APP, is furthermore provided by the present disclosure. The APP comprises executable instructions configured to be executed on an auxiliary device to implement a user interface for a system described above in the 'detailed description of embodiments', and in the claims. The APP may be configured to run on cellular phone, e.g. a smartphone, or on another portable device allowing communication with said system.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the system and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

Figure 1:
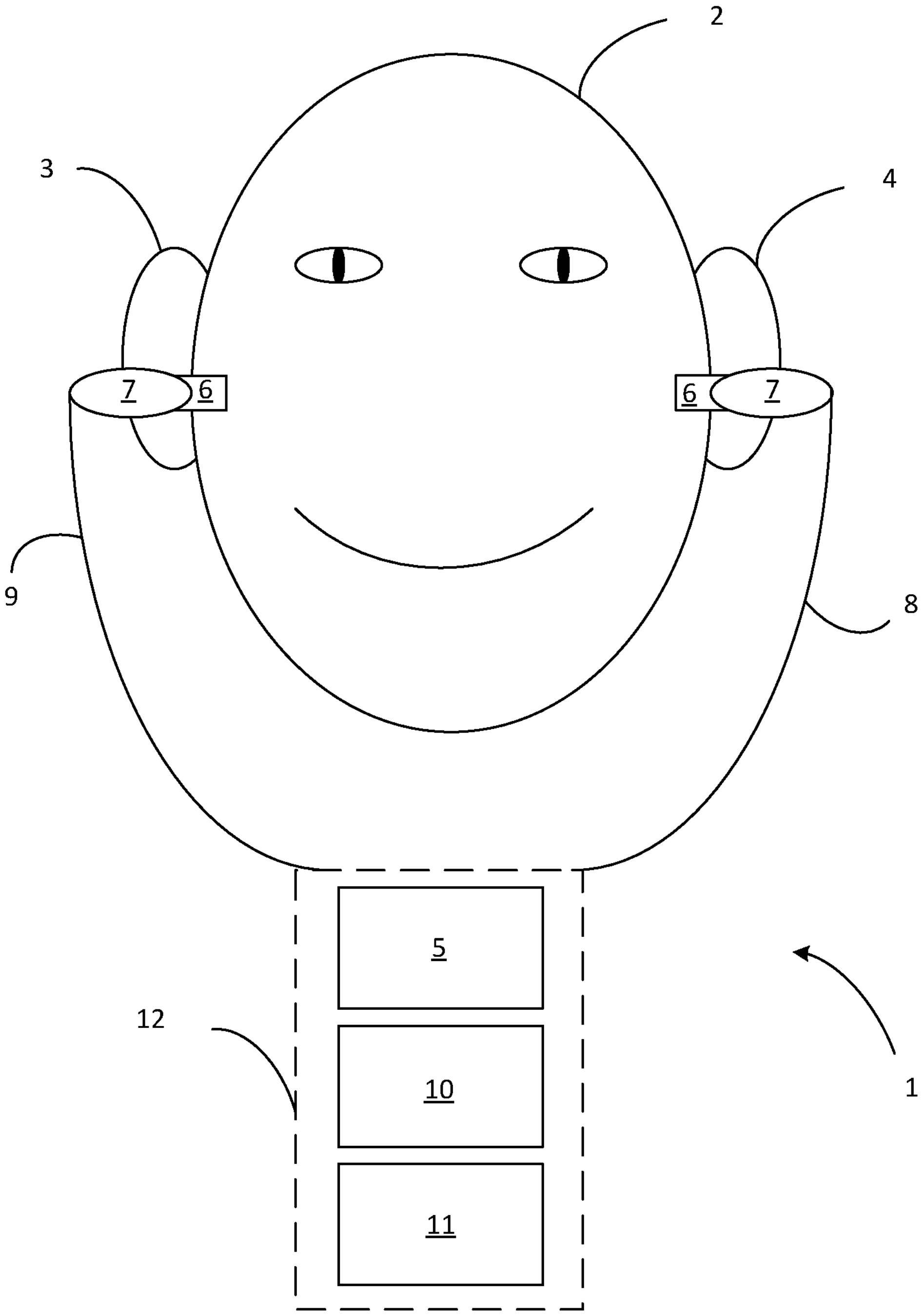
FIG. 1 shows an exemplary application scenario of a system according to the present disclosure.

FIG. 1 shows an exemplary application scenario of a system according to the present disclosure.

In FIG. 1, a system 1 for diagnosing cochlear hydrops of a person 2 is shown.

The system 1 may comprise an acoustic stimulus generating unit. The acoustic stimulus generating unit may be configured to provide an audio stimulus to at least one of the ears of the person 2. In FIG. 1, it is shown that the audio stimulus may be provided to both a first ear 3 and a second ear 4 of the person 2.

The acoustic stimulus generating unit may comprise a stimulus generator 5. The stimulus generator 5 may provide the audio stimulus.

The acoustic stimulus generating unit may comprise an ear-contacting part 6 and an output transducer 7. Instead, the acoustic stimulus generating unit may comprise a loudspeaker or a headset. The output transducer 7 may be arranged in the ear-contacting part 6. The ear-contacting part 6 may have an outer surface with a shape configured to fit the surface of the ear canal of the person 2. The ear-contacting part 6 may comprise a flexible material so that the ear-contacting part 6 may fit closely into the ear canal of the person 2.

The acoustic stimulus generating unit may provide an audio stimulus by the stimulus generator 5 to the first ear 3 and/or the second ear 4 of the person 2 via the output transducer 7 arranged in the ear-contacting part 6.

In FIG. 1, the stimulus generator 5 may be connected (e.g. operationally connected) to the output transducer 7 through a wired connection, e.g. a first wired connection 8 and a second wired connection 9. Alternatively, the stimulus generator 5 may be connected to the output transducer 7 through a wireless connection.

The stimulus generator 5 of the acoustic stimulus generating unit may be configured to provide a plurality of audio stimuli to the first ear 3 and/or the second ear 4 of the person 2, e.g. in an alternating manner. The plurality of audio stimuli may comprise at least one click audio stimulus and at least one chirp audio stimulus. Alternatively, the plurality of audio stimuli may comprise at least a first chirp audio stimulus and at least a second chirp audio stimulus.

The system 1 may comprise a recording unit 10. The recording unit 10 may be configured to record one or more auditory electrophysiological responses (e.g. an ABR) of the person 2 in response to the audio stimulus, or plurality of audio stimuli, being provided by the acoustic stimulus generating unit to at least one of the ears of the person 2. The recording of auditory electrophysiological response may be carried out automatically by the recording unit 10 and/or manually by a second person operating the system on the person 2.

The system 1 may comprise a diagnostic unit 11. The diagnostic unit 11 may be configured to process the recorded auditory electrophysiological responses. The diagnostic unit 11 may be configured to provide a diagnosis of cochlear hydrops of the person 2 based on the at least one click audio stimulus and at least one chirp audio stimulus, or based on the at least first chirp audio stimulus and at least second chirp audio stimulus, provided by the stimulus generator 5 to the first ear 3 and/or the second ear 4 of the person 2.

In FIG. 1, it is shown that the stimulus generator 5, the recording unit 10, and the diagnostic unit 11 may be arranged in the same apparatus 12, whereby generating the audio stimulus, measuring the resulting auditory electrophysiological responses, and diagnosing cochlear hydrops may be carried out with use of one apparatus 12. Thereby, a faster and easier diagnosis of cochlear hydrops may be provided.

Figure 2:
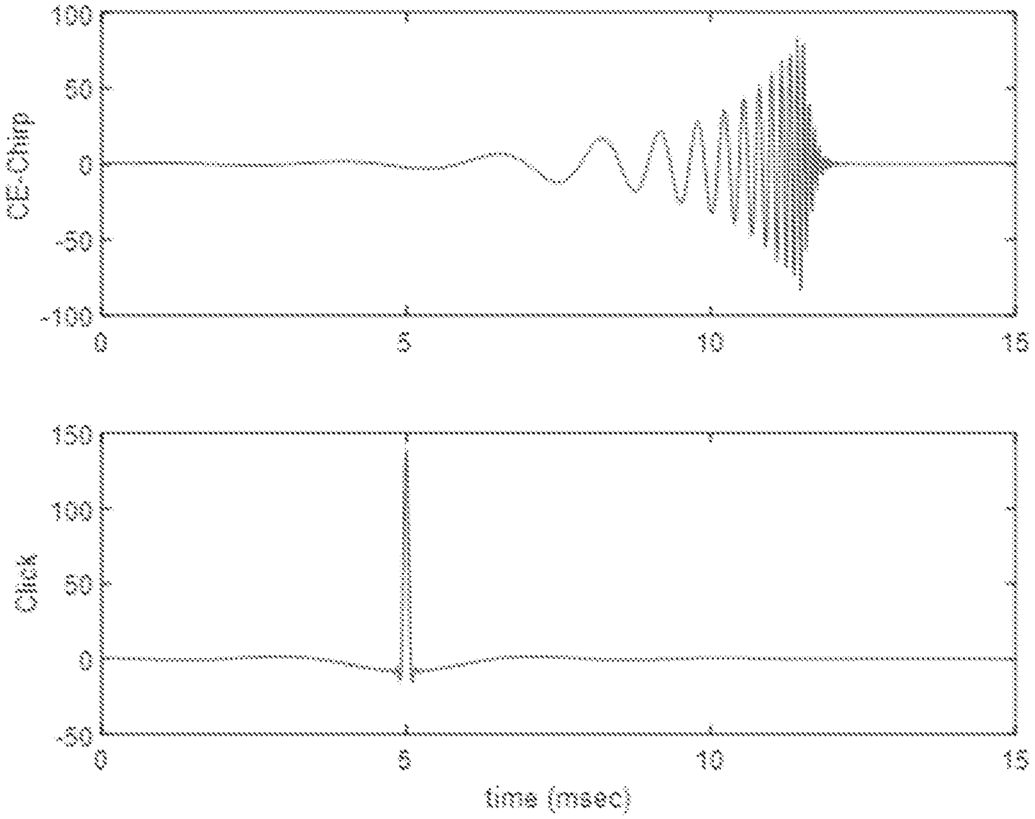
FIG. 2 shows an exemplary click and chirp audio stimulus according to the present disclosure.

FIG. 2 shows an exemplary click and chirp audio stimulus according to the present disclosure.

In FIG. 2, the top graph shows a chirp audio stimulus waveform, e.g. a CE-chirp audio stimulus. The amplitude of the chirp audio stimulus is shown as function of time in milliseconds.

In FIG. 2, the lower graph shows a click audio stimulus waveform. The amplitude of the click audio stimulus is shown as function of time in milliseconds.

Figure 3:
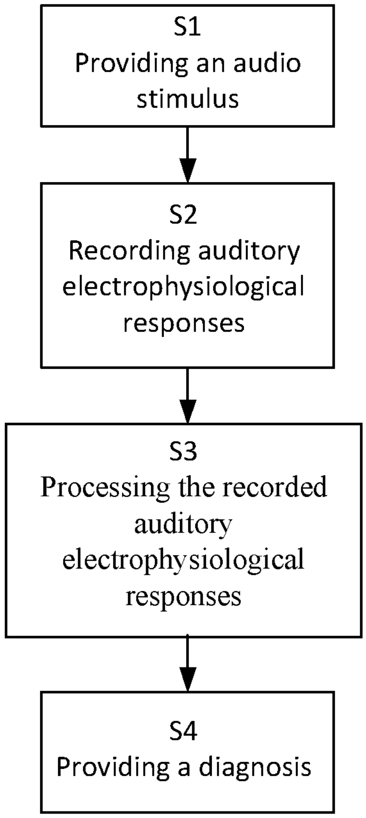
FIG. 3 shows an exemplary flow diagram of a method of recording an auditory electrophysiological response of a person or an animal.

FIG. 3 shows an exemplary flow diagram of a method of recording one or more auditory electrophysiological response of a person or an animal.

In FIG. 3, the method of recording auditory electrophysiological responses of a person or an animal may be recorded in response to providing at least one audio stimulus to at least one of the ears of the person or animal.

The method may comprise providing an audio stimulus S1.

The audio stimulus may comprise at least one click audio stimulus and at least one chirp audio stimulus, or may comprise at least a first chirp audio stimulus and at least a second chirp audio stimulus. The audio stimuli may be provided by a stimulus generator of an acoustic stimulus generating unit. The audio stimuli may be provided to at least one of the ears (e.g. to both) of the person or animal via an output transducer of the acoustic stimulus generating unit.

The method may comprise recording one or more auditory electrophysiological responses S2 of the person or animal.

The auditory electrophysiological response may be recorded by a recording unit, in response to the audio stimulus being provided by the acoustic stimulus generating unit to at least one of the ears of the person or animal.

The method may comprise processing the recorded one or more auditory electrophysiological responses S3.

The processing the recorded auditory electrophysiological responses S3 may be carried out by a diagnostic unit.

The method may comprise providing a diagnosis S4 of cochlear hydrops of the person or animal.

The providing of a diagnosis S4 of cochlear hydrops may be carried out by a diagnostic unit.

The diagnostic unit may provide the diagnoses based on the audio stimuli. The diagnostic unit may provide the diagnoses based on the recorded auditory electrophysiological responses.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein but are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

[1] Roeser, R. J., Valente, M., & Hosford-Dunn, H. (2007). Audiology: Diagnosis (Second edition). Thieme.

[2] Don, M., Kwong, B., & Tanaka, C. (2005). A Diagnostic test for Ménière's disease and cochlear hydrops: Impaired high-pass noise masking of auditory brainstem responses. Otology & Neurotology, 26, 711-722.

[3] Elberling, C., & Don, M. (2008). Auditory brainstem responses to a chirp stimulus designed from derived-band latencies in normal-hearing subjects. The Journal of the Acoustical Society of America, 124(5), 3022. https://doi.org/10.1121/1.2990709

[4] Elberling, C., & Don, M. (2010). A direct approach for the design of chirp stimuli used for the recording of auditory brainstem responses. The Journal of the Acoustical Society of America, 128(5), 2955. https://doi.org/10.1121/1.3489111

The invention claimed is:

1. A system for diagnosing cochlear hydrops of a person or an animal, the system comprising:

an acoustic stimulus generating unit comprising a stimulus generator and an output transducer, where the acoustic stimulus generating unit is configured to provide an audio stimuli by the stimulus generator to at least one of the ears of the person or animal via the output transducer, wherein the audio stimuli comprises a first click audio stimulus and a first chirp audio stimulus, an earpiece configured to be inserted into an ear canal of the person or animal, the earpiece being made of a material configured to conform with the shape of the wall of the ear canal of the person or animal, wherein the output transducer is operably arranged within the earpiece, at least one electrode configured to be arranged at the skin of the person or animal, wherein the at least one electrode is configured to measure auditory electrophysiological responses of the person or animal in response to the audio stimuli being provided by the acoustic stimulus generating unit to at least one of the ears of the person or animal, a recording unit configured to record the measured auditory electrophysiological responses of the person or animal in response to the audio stimuli being provided by the acoustic stimulus generating unit to at least one of the ears of the person or animal, and an auditory diagnostic unit configured to generate a cochlear hydrops diagnosis by processing the recorded auditory electrophysiological responses, and output the cochlear hydrops diagnosis, wherein the auditory diagnostic unit being configured to process the recorded auditory electrophysiological responses, comprises the auditory diagnostic unit being configured to compare response characteristics of the recorded auditory electrophysiological responses based on the first click audio stimulus and the first chirp audio stimulus, the response characteristics being respective wave V amplitudes.

2. The system according to claim 1, wherein the auditory diagnostic unit is configured to compare the response characteristics by determining a ratio between two wave V amplitudes respectively associated with the first click audio stimulus and the first chirp audio stimulus, respectively.

3. The system according to claim 2, wherein the acoustic stimulus generating unit is configured to provide the first click audio stimulus and the first chirp audio stimulus at a fixed suprathreshold level.

4. The system according to claim 3, wherein at least one of the first click audio stimulus and first chirp audio stimulus is frequency shaped based on a hearing threshold level (HTL) of the person or animal.

5. The system according to claim 1, wherein the acoustic stimulus generating unit is configured to provide the first click audio stimulus and the first chirp audio stimulus at a fixed suprathreshold level.

6. The system according to claim 1, wherein at least one of the first click audio stimulus and first chirp audio stimulus is frequency shaped based on a hearing threshold level (HTL) of the person or animal.

7. The system according to claim 6, wherein the at least one of the first click audio stimulus and first chirp audio stimulus is provided at a fixed sensation level (SL) above the HTL of the person or animal at multiple frequencies within a range of stimulus frequencies.

8. The system according to claim 5, wherein the acoustic stimulus generating unit is configured to provide the first click audio stimulus and the first chirp audio stimulus at a fixed suprathreshold level.

9. The system according to claim 1, wherein the acoustic stimulus generating unit is configured to provide the audio stimuli in an alternating manner to at least one of the ears of the person or animal.

10. The system according to claim 1, wherein the acoustic stimulus generating unit is configured to provide the audio stimuli at a plurality of sound pressure levels to at least one of the ears of the person or animal.

11. The system according to claim 1, wherein the auditory diagnostic unit is configured to provide respective averages of the response characteristics of the recorded auditory electrophysiological responses based on the first click audio stimulus and first chirp audio stimulus, respectively.

12. The system according to claim 1, wherein the auditory electrophysiological responses are auditory brain-stem responses.

13. A method of diagnosing cochlear hydrops in a person or animal, the method comprising:

providing audio stimuli comprising a first click audio stimulus and a first chirp audio stimulus, by a stimulus generator of an acoustic stimulus generating unit to at least one of the ears of the person or animal via an output transducer of the acoustic stimulus generating unit, the output transducer being operably arranged in an earpiece inserted into an ear canal of the person or animal, the earpiece being made of a material conforming to the shape of the wall of the ear canal, measuring, via at least one electrode arranged at the skin of the person or animal, auditory electrophysiological responses of the person or animal in response to the audio stimuli being provided by the acoustic stimulus generating unit to at least one of the ears of the person or animal, recording, by a recording unit, the measured auditory electrophysiological responses of the person or animal, in response to the audio stimuli being provided by the acoustic stimulus generating unit to at least one of the ears of the person or animal, and generating a cochlear hydrops diagnosis by processing the recorded auditory electrophysiological responses, by an auditory diagnostic unit, based on the first click audio stimulus and the first chirp audio stimulus, and outputting the cochlear hydrops diagnosis, wherein processing the recorded auditory electrophysiological responses comprises comparing response characteristics of the recorded auditory electrophysiological responses based on the first click audio stimulus and the first chirp audio stimulus, the response characteristics being respective wave V amplitudes.

14. The method according to claim 13, wherein the method comprises measuring a hearing threshold level (HTL) of at least one of the ears of the person or animal.

15. The method according to claim 13, wherein the comparing comprises determining a ratio between two wave V amplitudes respectively associated with the first click audio stimulus and the first chirp audio stimulus.

16. The method according to claim 13, wherein the acoustic stimulus generating unit provides the audio stimuli in an alternating manner to at least one of the ears of the person or animal.

17. The method according to claim 13, wherein the audio stimuli have a specified frequency bandwidth, presentation rate, amplitude, and spectral content.

* * * * *